United States Patent
Gettig et al.

(10) Patent No.: US 6,190,361 B1
(45) Date of Patent: Feb. 20, 2001

(54) SELECTIVELY LOCKABLE NEEDLE GUARD

(75) Inventors: William A. Gettig; Larry E. Shook, both of Millheim, PA (US)

(73) Assignee: Gettig Technologies, Inc., Spring Mills, PA (US)

( * ) Notice: Under 35 U.S.C. 154(b), the term of this patent shall be extended for 0 days.

(21) Appl. No.: 09/551,063

(22) Filed: Apr. 18, 2000

(51) Int. Cl.$^7$ ...................................... A61M 5/00
(52) U.S. Cl. ........................ 604/192; 604/110; 604/195
(58) Field of Search .................................. 604/192, 110, 604/187, 198, 263, 195

(56) References Cited

U.S. PATENT DOCUMENTS

| | | |
|---|---|---|
| Re. 34,045 | 8/1992 | McFarland . |
| 1,793,068 | 2/1931 | Dickinson . |
| 1,845,036 | 2/1932 | Susher . |
| 2,047,010 | 7/1936 | Dickinson . |
| 2,574,964 | 11/1951 | Eisenstark . |
| 2,925,083 | 2/1960 | Craig . |
| 3,640,278 | 2/1972 | Friedman . |
| 4,425,120 | 1/1984 | Sampson et al. . |
| 4,631,057 | 12/1986 | Mitchell . |
| 4,655,751 | 4/1987 | Harbaugh . |
| 4,681,567 | 7/1987 | Masters et al. . |
| 4,693,708 | 9/1987 | Wanderer et al. . |
| 4,702,738 | 10/1987 | Spencer . |
| 4,723,943 | 2/1988 | Spencer . |
| 4,725,267 | 2/1988 | Vaillancourt . |
| 4,731,059 | 3/1988 | Wanderer et al. . |
| 4,737,144 | 4/1988 | Choksi . |
| 4,738,663 | 4/1988 | Bogan . |
| 4,743,233 | 5/1988 | Schneider . |
| 4,767,413 | 8/1988 | Haber et al. . |
| 4,801,295 | 1/1989 | Spencer . |
| 4,804,372 | 2/1989 | Laico et al. . |
| 4,816,022 | 3/1989 | Poncy . |
| 4,826,490 | 5/1989 | Byrne et al. . |
| 4,842,587 | 6/1989 | Poncy . |
| 4,846,796 | 7/1989 | Carrell et al. . |
| 4,850,994 | 7/1989 | Zerbst et al. . |
| 4,863,436 | 9/1989 | Glick . |
| 4,874,383 | 10/1989 | McNaughton . |
| 4,892,521 | 1/1990 | Laico et al. . |
| 4,894,055 | 1/1990 | Sudnak . |
| 4,897,083 | 1/1990 | Martell . |
| 4,898,590 | 2/1990 | Andors . |
| 4,915,701 | 4/1990 | Halkyard . |
| 4,923,447 | 5/1990 | Morgan . |
| 4,927,417 | 5/1990 | Moncada et al. . |

(List continued on next page.)

FOREIGN PATENT DOCUMENTS

| | | |
|---|---|---|
| 813433 | 7/1949 | (DE) . |
| 924734 | 5/1963 | (DE) . |
| 0586199 | 3/1994 | (EP) . |
| 1233302 | 5/1971 | (GB) . |
| 2059268 | 4/1981 | (GB) . |
| 2114006 | 8/1983 | (GB) . |
| 2225723 | 6/1990 | (GB) . |
| 2289223 | 11/1995 | (GB) . |
| 98/10816 | 3/1998 | (WO) . |

*Primary Examiner*—John D Yasko
(74) *Attorney, Agent, or Firm*—Kirkpatrick & Lockhart LLP

(57) ABSTRACT

A needle guard assembly for a syringe adapted to receive a hypodermic needle assembly. The guard assembly includes a needle guard that is slidably mounted on a needle-supporting hub. The needle guard may be moved from a latched position wherein the needle is fully protected by the guard to a position wherein the injection end of the needle is exposed. The assembly further includes a locking mechanism for permanently locking the needle guard in an extended position over the needle to prevent further use of the needle and to facilitate safe disposal of the assembly.

24 Claims, 5 Drawing Sheets

U.S. PATENT DOCUMENTS

| | | |
|---|---|---|
| 4,935,010 | 6/1990 | Cox et al. . |
| 4,935,016 | 6/1990 | Deleo . |
| 4,961,730 | 10/1990 | Poncy . |
| 4,998,924 | 3/1991 | Ranford . |
| 5,019,051 | 5/1991 | Hake . |
| 5,026,354 | 6/1991 | Kocses . |
| 5,045,066 | 9/1991 | Scheuble et al. . |
| 5,137,521 | 8/1992 | Wilkins . |
| 5,160,326 | 11/1992 | Talonn et al. . |
| 5,176,657 | 1/1993 | Shields . |
| 5,197,953 | 3/1993 | Colonna . |
| 5,226,894 | 7/1993 | Haber et al. . |
| 5,250,037 | 10/1993 | Bitdinger . |
| 5,254,100 | 10/1993 | Huband . |
| 5,267,977 | 12/1993 | Feeney, Jr. . |
| 5,292,314 | 3/1994 | D'Alessio et al. . |
| 5,312,347 | 5/1994 | Osborne et al. . |
| 5,324,272 | 6/1994 | Smedley et al. . |
| 5,358,489 | 10/1994 | Wyrick . |
| 5,389,085 | 2/1995 | D'Alessio et al. . |
| 5,498,244 | 3/1996 | Eck . |
| 5,540,664 | 7/1996 | Wyrick . |
| 5,558,648 | 9/1996 | Shields . |
| 5,562,625 | 10/1996 | Stefancin, Jr. . |
| 5,609,584 | 3/1997 | Gettig et al. . |
| 5,713,873 | 2/1998 | Jehle . |
| 5,817,064 | 10/1998 | DeMarco et al. . |
| 5,833,669 | 11/1998 | Wyrick . |
| 5,865,818 | 2/1999 | Gould . |

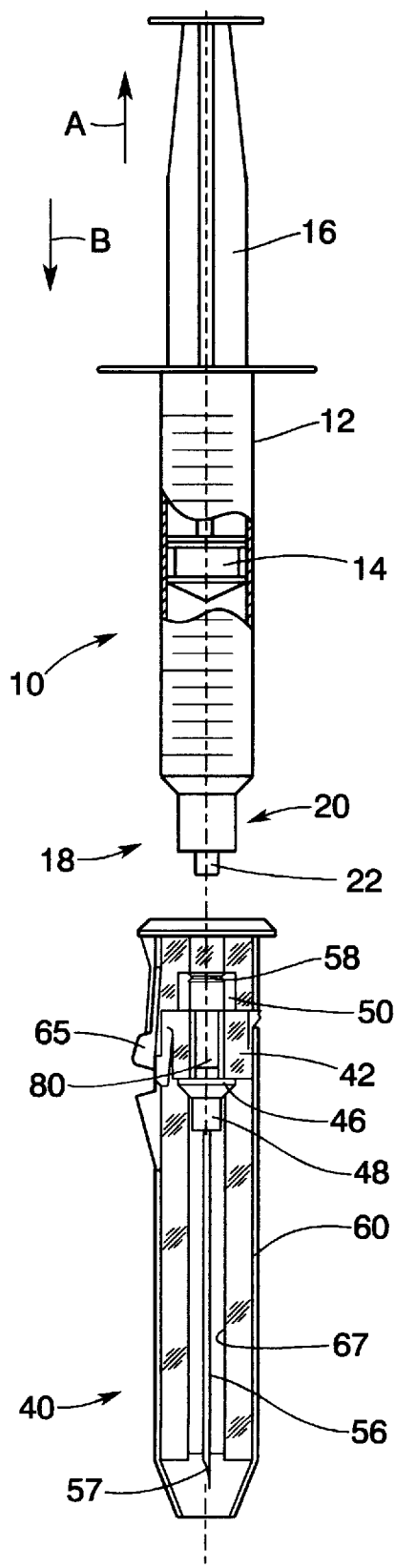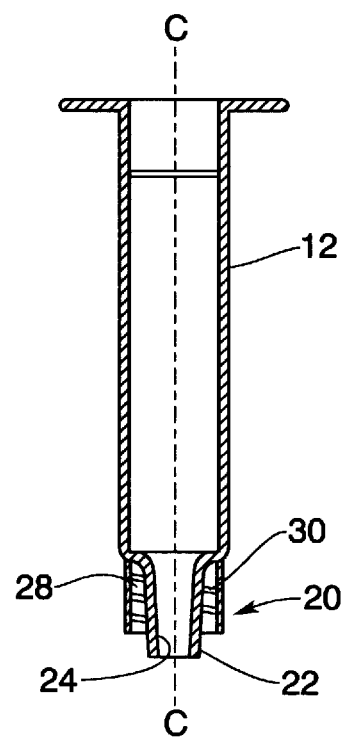
Fig.1
Fig.1A

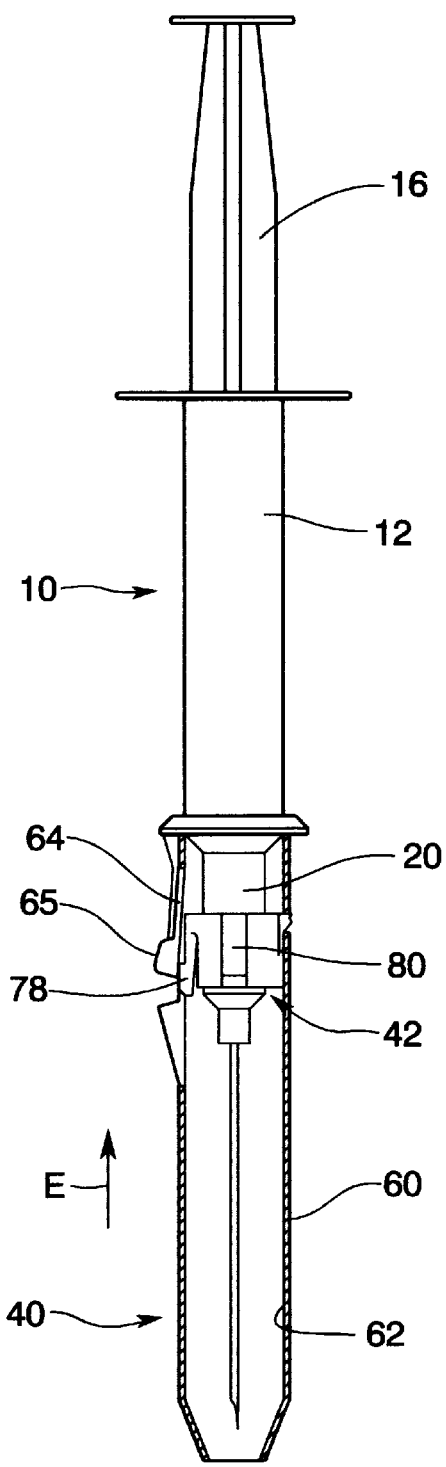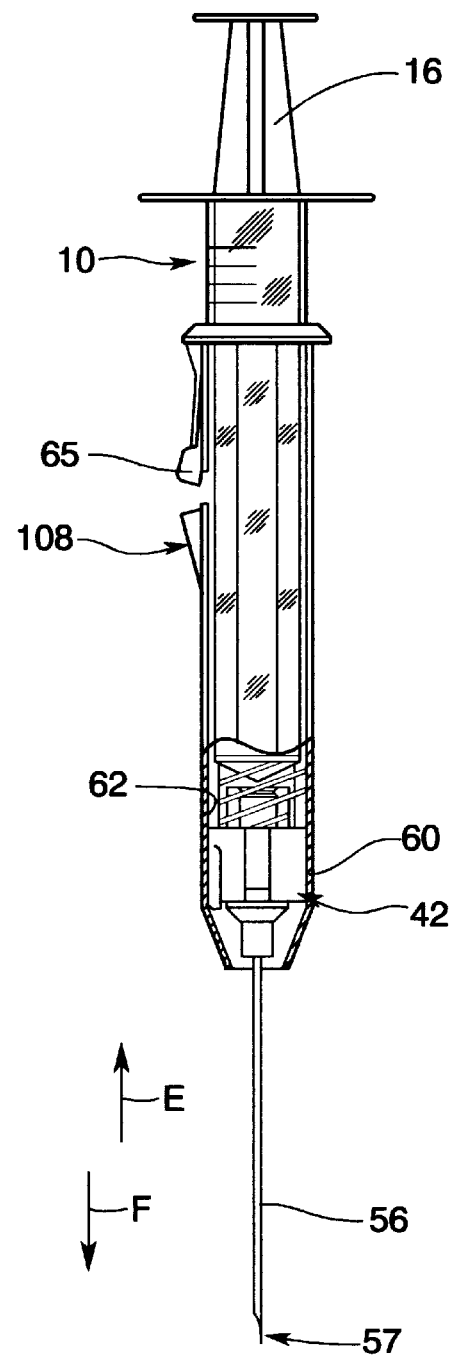
Fig.2
Fig.3

SELECTIVELY LOCKABLE NEEDLE GUARD

CROSS-REFERENCE TO RELATED APPLICATIONS

Not applicable.

FEDERALLY SPONSORED RESEARCH

Not applicable.

BACKGROUND OF THE INVENTION

1. Field of the Invention

The subject invention relates to medical devices and, more particularly, to hypodermic syringes with protective needle guards.

2. Description of the Invention Background

Syringes equipped with hypodermic needles are commonly used to inject precise amounts of medicament subcutaneously. In the past, hypodermic needles were provided with a removable needle shield that encased the needle prior to use. To use the syringe, the shield was removed from the needle and retained by the user so that it could be replaced after the injection had been completed. Replacement of the shield on the contaminated needle was fraught with risk and required extreme care on the user's part to avoid inadvertent sticks by the contaminated needle. Furthermore, if the user lost or misplaced the shield during the injection process or otherwise failed to replace it after use, the syringe was disposed of with an exposed contaminated needle.

Over the years, healthcare professionals recognized these problems and consequently several different types of needle guards were developed. For example, U.S. Pat. No. 2,571,653 to Bastein, U.S. Pat. No. 4,631,057 to Mitchell, U.S. Pat. No. 4,725,267 to Vaillancourt, U.S. Pat. No. 4,731,059 to Wanderer et al., and U.S. Pat. No. 4,804,372 to Laico et al. all disclose various types of needle shield arrangements that are mounted on a portion of the syringe and that purport to eliminate the problems associated with replacing the guard after the needle has been used. While many of such inventions effectively addressed the problems of inadvertent needle sticks, such inventions were often difficult to economically fabricate and/or difficult to use. Thus, they were not readily embraced by the healthcare community.

Existing needle guard assemblies also have other shortcomings. For example, many of such guards are slidably supported on the syringe, but lack a mechanism for retaining the needle guard in its extended position wherein it fully protects the needle. However, the needle guard disclosed in U.S. Pat. No. 5,609,584 to Gettig et al. solved such problem. Such shield could be easily retracted to expose the needle for injection purposes and thereafter be extended over the needle and releasably retained in that position until needed for the next injection or until the needle was disposed of.

In recent years, however, with the increasing concerns regarding the spread of diseases such as AIDS and hepatitis through inadvertent needle sticks, some governmental agencies have recognized the desirability of a needle guard that can be releasably latched in a needle-guarding position between the time the medicament is drawn into the syringe and the time the medicament is injected into the patient or between consecutive injections into the same patient while also having the ability to permanently lock the guard in the needle-guarding position for safe disposal of the needle.

Thus, there is a need for a guard for a hypodermic needle that can be releasably latched in a needle-guarding position between injections and that also has the capability of being permanently locked in such position to render the needle unusable for further injections and for safe disposal thereof.

There is a further need for a needle guard having the above-mentioned attributes that can be economically manufactured and is easy and safe to use.

Yet another need exists for a needle guard assembly that has the above-mentioned attributes and that can be readily constructed for use with a variety of types and sizes of syringes.

SUMMARY OF THE INVENTION

In accordance with one form of the present invention, there is provided a needle assembly for a syringe. The needle assembly includes a needle-supporting hub that is attachable to the body of the syringe. A latch assembly is formed in the hub and a hollow needle guard is slidably supported on the hub. The needle guard is selectively movable between a first extended position covering the needle and a second retracted position wherein the injection end of the needle is exposed. A latch opening is provided in the needle guard through which a portion of the latch assembly can extend. The latch assembly is selectively biasable between a first engaged position wherein a portion of the latch assembly is received in the latch opening to retain the needle guard in the first extended position and a second disengaged position wherein the portion of the latch assembly is biased out of the latch opening to enable the needle guard to be moved to the second retracted position. The needle assembly further includes a locking mechanism that is formed in the hollow needle guard. The locking mechanism is selectively biasable between a first, unlocked position and a second locked position wherein a portion of the locking mechanism engages a portion of the latch assembly to permanently retain the needle guard in the first extended position.

It is a feature of the present invention to provide a guard for a hypodermic needle that can be releasably latched in a needle-guarding position between injections and that also has the capability of being permanently locked in such position to render the needle unusable for further injections and for safe disposal thereof.

It is another feature of the present invention to provide a needle guard having the above-mentioned attributes that can be economically manufactured and easy to use.

It is still another feature of the present invention to provide a needle guard assembly that has the above-mentioned attributes and that can be readily constructed for use with a variety of syringe arrangements.

Accordingly, the present invention provides solutions to the shortcomings of prior needle guard arrangements. Those of ordinary skill in the art will readily appreciate, however, that these and other details, features and advantages will become further apparent as the following detailed description of the embodiments proceeds.

BRIEF DESCRIPTION OF THE DRAWINGS

In the accompanying Figures, there are shown present embodiments of the invention wherein like reference numerals are employed to designate like parts and wherein:

FIG. 1 is an exploded view of a needle guard assembly of the present invention and a conventional syringe;

FIG. 1A is a cross-sectional view of the syringe body of the syringe depicted in FIG. 1;

FIG. 2 is a partial cross-sectional view of the needle guard assembly depicted in FIG. 1 attached to the syringe depicted in FIG. 1 with the needle guard in the first extended or latched position;

FIG. 3 is another partial cross-sectional view of the needle guard assembly and syringe depicted in FIG. 2 with the needle guard in a second retracted or unlatched position;

DETAILED DESCRIPTION OF THE EMBODIMENTS OF THE INVENTION

Figure 6:
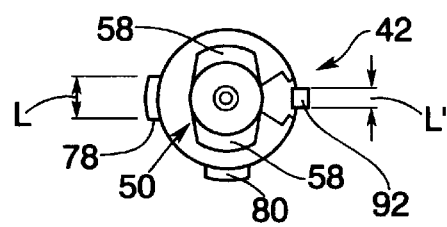
FIG. 6 is a top view of the needle-supporting hub assembly depicted in FIGS. 4 and 5.

Referring now to the drawings for the purposes of illustrating the present embodiments of the invention only and not for the purposes of limiting the same, the Figures show a selectively lockable needle guard assembly 40 adapted for use in connection with a syringe 10. Syringe 10 has a hollow syringe body 12 that supports a piston 14 therein. See FIG. 1. The piston 14 is attached to a plunger rod 16 that is used to actuate the piston 14 within the body 12 for drawing medicament into the syringe or discharging it therefrom. The forward end 18 of the syringe body 12 has a conventional "luer-lock" attachment portion 20 formed thereon. Such luer-lock connections are known in the art and generally comprise a tapered nose 22 that has a passageway 24 therethrough that communicates with the interior of the syringe body 12. Thus, by pulling the plunger rod in the "A" direction, a medicament may be drawn into the body 12 of the syringe 10 through the passageway 24 in the nose 22. The medicament drawn into the syringe body 12 may be expelled therefrom by pushing the plunger rod 16 into the syringe body 12 in the "B" direction in a known manner. See FIG. 1.

As can be seen in FIG. 1A, the tapered nose 22 is coaxially aligned along axis C—C and protrudes a short distance out of the forward portion 18 of the syringe body 12. To facilitate removable attachment of the syringe 10 to a conventional port arrangement or cannula carrier, a threaded socket 28 is formed in the forward portion 18. The threads 30 are adapted to engage threads or ears that protrude from the port or fixture to which it is attached syringes of the type depicted in FIGS. 1–3 are manufactured by Terumo Medical Corporation of Elkton, Md. 21921 under the Terumo® trademark. In the following example, the needle guard assembly 40 of the present invention is described for use with a commercially available 3 mm syringe. Thus, the specific sizes and dimensions of certain components comprising various embodiments of the needle guard assembly 40 described below are particularly suited for that size and style of syringe. However, as will be discussed in further detail below, the subject invention could be successfully employed in connection with a variety of other types and sizes of syringes without departing from the spirit and scope of the present invention. Accordingly, the present invention should not be limited solely to a construction that is adapted for use in connection with 3 mm syringes and/or in connection with syringes having luer-lock tips.

As can be seen in FIGS. 1–6, one embodiment of the needle guard assembly 40 of the present invention includes a needle-supporting hub 42 that may be fabricated from a polymeric material such as, for example, nylon. The needle-supporting hub 42 has a body portion 44 that includes a central portion 46, a needle-supporting nose portion 48, and a syringe attachment portion 50. The nose portion 48 has a first axial passageway 52 formed therein that is coaxially aligned on a central axis D—D. See FIG. 4. In this embodiment, a second tapered passageway 54 is coaxially aligned with the first passageway 52 and is adapted to achieve a fluid-tight sliding fit with the nose 22 of the syringe 10. It will be appreciated that the taper of the second passageway 54 corresponds with the taper of the nose 22 so as to achieve a fluid-tight seal therebetween when the nose 22 is inserted into the passageway 54.

The first passageway 52 is sized to receive a conventional hypodermic needle 56 therein. Needle 56 is retained within the first passageway by an adhesive bond in a manner known in the art which also serves to create a fluid-tight seal between the needle 56 and the hub 42.

The hub 42 may be removably attachable to the syringe body 12 by the syringe attachment portion 50. The syringe attachment portion 50 includes a pair of outwardly protruding ears 58 that are adapted to engage the threads 30 in the threaded socket 28 of the syringe 10 in a known manner. While this embodiment of the invention includes a needle-supporting hub 42 that is removably attachable to the syringe 10, those of ordinary skill in the art will appreciate that the needle-supporting hub 42 could conceivably be integrally formed with the syringe body 12 or be non-removably attached to the syringe body 12 by a conventional adhesive or other permanent mechanical attachment arrangement.

The needle guard assembly 40 also includes a hollow needle guard 60 that is slidably supported on the needle-supporting hub 42. In this embodiment, the needle guard 60 is slidably mounted on the needle-supporting hub 42 such that it may be selectively moved between a first extended or "latched" position wherein the injection end 57 of the needle 56 is completely received within the hollow needle guard 60 (FIG. 2) and a second position wherein the injection end 57 of the needle 56 is exposed (FIG. 3). The artisan of ordinary skill will appreciate, however, that the hollow needle guard 60 may be moved to various positions between the first and second positions illustrated in FIGS. 2 and 3 to vary the amount of needle 56 that protrudes out of the guard 60.

The needle guard 60 may be fabricated from transparent polymer material such as, for example, PETG (Polyethylene Terephthalate Copolymer Glycol). However, the needle guard 60 could be fabricated from a variety of other materials. The hollow needle guard 60 has a passage 62 therethrough that is sized to permit the guard 60 to extend over the syringe body 12 when the guard 60 is moved to the second position or other intermediate "unlatched" positions. See FIG. 3.

In this embodiment, a latch assembly 70 enables the hollow needle guard 60 to be selectively latched in the first extended position to protect the user from inadvertent needle sticks between injections. Furthermore, as will be discussed in further detail below, the needle guard assembly 40 of the present invention also includes a locking mechanism 100 that enables the needle guard 60 to be permanently locked in its fully extended position after all injections have been completed to render the needle assembly 40 unusable for performing further injections and safe for disposal purposes. Thus, as used herein, the term "permanently" means that the device 40 has been placed in a condition that effectively renders it unusable for performing further injections, absent the application of some exceptional or extraordinary force applied to the locking mechanism.

Figure 4:
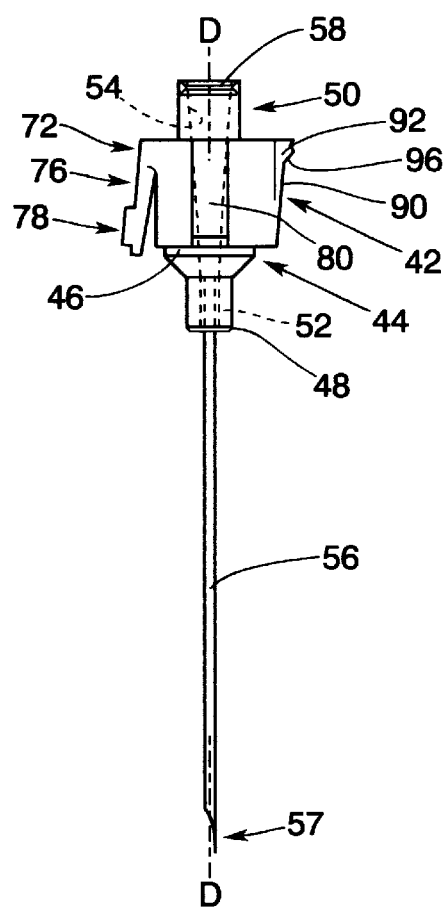
FIG. 4 is side view of a needle-supporting hub assembly of the present invention.
Figure 5:
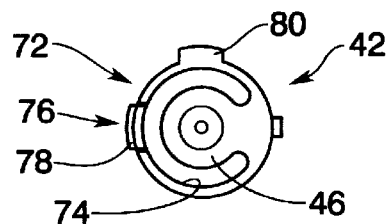
FIG. 5 is a bottom view of the needle-supporting hub assembly depicted in FIG. 4.

As can be seen in FIGS. 4–6, the hub 42 has an outer wall portion 72 that is spaced-apart from the central portion 46 of the hub 42 and defines a semi-annular cavity 74 therebetween. See FIG. 5. In this embodiment, the latch assembly 70 comprises a cantilevered latch flap 76 formed in the outer wall portion 72 of the hub 42. A latch tab 78 is formed on the outer end of the latch flap 76 and is adapted to be selectively received in a latch opening 62 in the hollow needle guard 60 when the needle guard 60 is in the first extended position. See FIGS. 7–9. Also in this embodiment, a cantilevered actuator flap 64 is integrally formed in the wall 63 of the needle guard 60 and is oriented to register with the latch tab 78 when the needle guard 60 is in the first extended position. An actuator button 65 is formed on the outer end of the actuator flap 64 to enable the actuator flap 64 to be biased into contact with the latch tab 78 to displace the latch tab 78 out of the latch opening 62 in the needle guard 60. The reader will appreciate that, when the latch tab 78 is received within the latch opening 62, it retains the needle guard 60 in a latched position to prevent inadvertent movement of the needle guard 60 which could cause the injection end 57 of the needle 56 to be exposed. To expose the injection end 57 of the needle 56 for injection purposes or for loading medicament into the syringe, the user simply biases the actuator flap 64 into contact with the latch tab 78 to displace the latch tab 78 out of the latch opening 62 in the needle guard 60 (FIG. 9) and applies an axial force to the needle guard 60 in the "E" direction relative to the syringe body 12 to retract the needle guard 60 over the syringe body 12.

Figure 8:
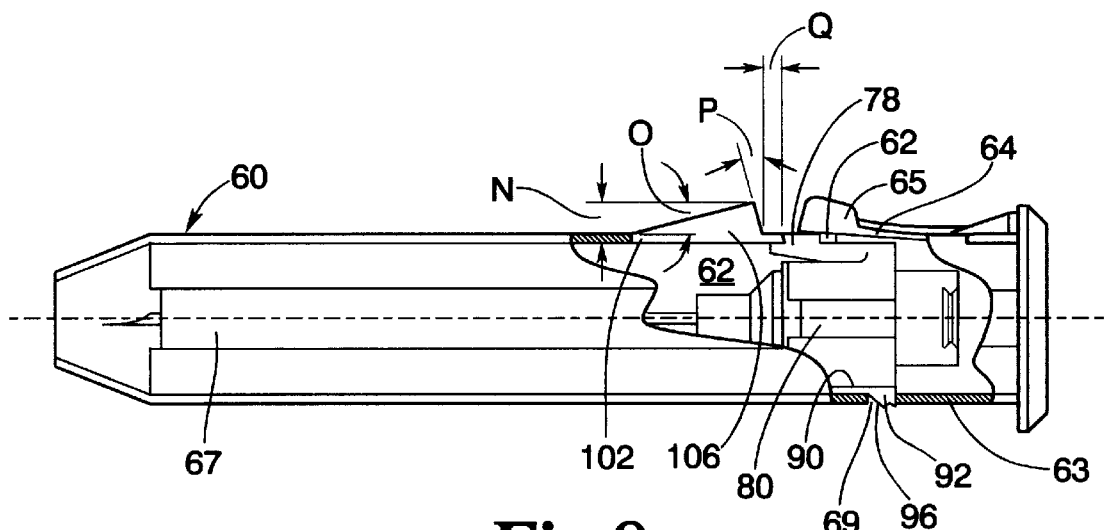
FIG. 8 is a partially cut away side view of the needle guard assembly of the present invention depicted in FIG. 7 in the latched position.
Figure 9:
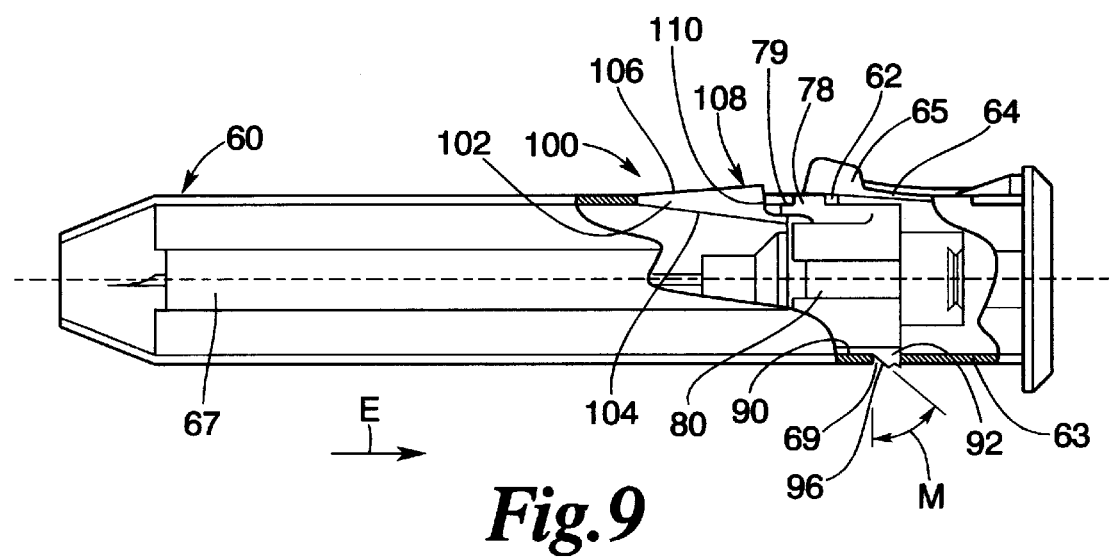
FIG. 9 is another partially cut away side view of the needle guard assembly depicted in FIGS. 7 and 8 wherein the guard has been permanently locked in an extended or latched position.

Also in this embodiment, an axial tab 80 is formed on a portion of the outer wall 72 of the hub 42 and is adapted to be slidably received in an axially extending recess or groove 67 integrally formed in the needle guard 60 as shown in FIGS. 8 and 9. The reader will appreciate that the axial tab 80 and axially extending recess 67 serve to prevent the needle guard 60 from rotating relative to the hub 42. It will be further appreciated that such configuration enables the hub 42 to be safely attached to the syringe 10 by applying a rotational force to the needle guard 60.

The hub assembly 42 may further include a cantilevered retainer flap 90 that is also formed in the outer wall portion 72 of the hub 42 as shown in FIG. 4. The retainer flap 90 may be diametrically opposed to the latch flap 64 on the outer wall 72 of the hub 42 (i.e., located 180° from each other). Also in this embodiment, a retainer tab 92 is formed on the outer end of the retainer flap 90. As can be seen in FIG. 5, the retainer tab 92 may be smaller than the latch tab 78 (i.e., the length "L" of the latch tab 78 is larger than the length "L'" of the retainer tab 92) and have a sloped forward edge 96. In one embodiment, the length "L" of the latch tab 78 is approximately 0.125 inches and the length "L'" of the retainer tab 92 is approximately 0.080 inches. The sloped forward edge 96 of the retainer tab 92 may be oriented at an angle "M" of approximately forty-five degrees. See FIG. 9.

Of course, these components may be provided in other suitable sizes. The retainer tab 92 is oriented to be received in a retainer opening 69 in the needle guard 60 when the latch tab 78 is received in the latch opening 62 to further retain the needle guard 60 in the first extended position. However, the sloped forward edge 96 serves to facilitate the movement of the retainer tab 92 out of the second opening 69 when an axial force is applied to the needle guard 60 in the "E" direction. Thus, in this embodiment, a second actuator tab is not required to bias the retainer tab 92 out of the retainer opening 69 in the needle guard 60.

The present invention also includes a locking mechanism 100 that cooperates with the latch assembly 70 to permanently prevent the needle guard 60 from being moved from the first extended position to another position wherein the injection end 57 of the needle 56 is exposed (i.e., protrudes out of the open forward end of the needle guard 60). In this embodiment, the locking mechanism 100 includes a cantilevered locking flap 102 integrally formed in the outer wall of the needle guard 60. Locking flap 102 may be 0.38 inches long (distance "M'" in FIG. 7). However, the locking flap 102 could be provided in other lengths and sizes. More specifically and with reference to FIGS. 7–9, the locking flap 102 (in an unactuated position) is substantially coplanar with the remaining portion of the wall of the needle guard 60. That is, when the locking flap 102 is unactuated as shown in FIG. 8, it does not extend into the passageway 62 extending through the needle guard 60 to thereby enable the needle guard 60 to slide over the syringe body 12. See FIG. 3. When in the latched position as shown in FIG. 8 (i.e., the needle guard 60 is releasably latched in an extended position, but is not permanently locked in position), the end of the locking flap 102 is received on a ledge 79 formed in the forward end of the latch tab 78.

Figure 7:
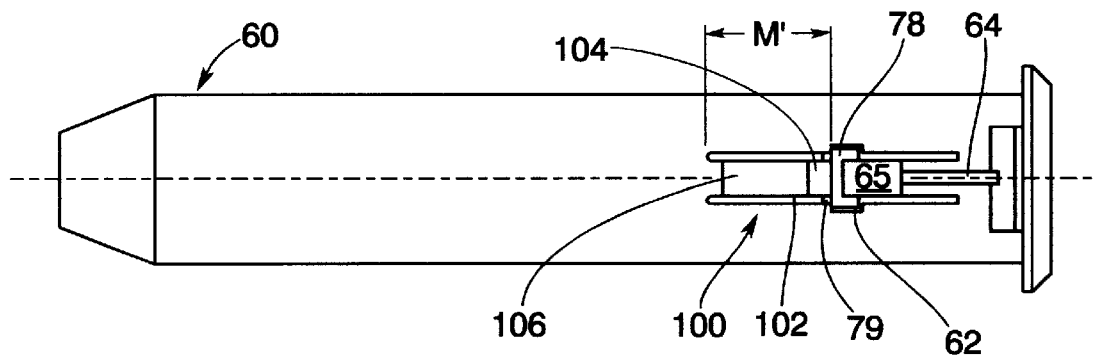
FIG. 7 is an enlarged top view of a needle guard assembly of the present invention in the first extended or latched position.

To permanently lock the needle guard 60 in the first extended position wherein further use of the needle 56 is prevented, the locking flap 102 is biased to the position shown in FIG. 9. As can be seen in that Figure, the forward portion of the locking flap 102 is biased under the ledge 79 portion of the latch tab 78 and serves to retain the latch tab 78 in latching engagement with the latch opening 62 in the needle guard 60. To facilitate such biasing of the locking flap 102 under the ledge 79 of the latch tab 78, a locking tab 106 is formed on the outer surface of the locking flap 102 as shown in FIGS. 7–9. In this embodiment, the locking tab 106 is provided in the shape of a ramp that has a sloped actuation surface 108 and a locking or abutment surface 110. In one embodiment, the locking tab 106 protrudes approximately 0.100 inches out from the inner surface of the needle guard wall (distance "N" in FIG. 8). It has been discovered that such size serves to provide the user with a sufficient amount of leverage to enable the locking flap 102 to be biased under the ledge 79 of the latch tab 78 with an acceptable amount of force. Also in this embodiment, the sloped actuation surface 108 is oriented at a slope of approximately nineteen degrees relative to the outer surface of the needle guard (angle "O" in FIG. 8) and the locking or abutment surface 110 surface is oriented at an angle of approximately ten degrees from vertical (angle "P" in FIG. 8). Also in this embodiment, the forward ledge 79 in the hub latch tab 78 is approximately 0.035 inches long and approximately 0.032 inches thick. The portion of the locking flap 102 adapted to be biased under the ledge may be approximately 0.060 long (distance "Q" in FIG. 8) and approximately 0.030 thick. However, the size and shape of such components may be altered to suit the particular size and shape of the syringe with which the needle assembly is to be used. Those of ordinary skill in the art will further appreciate that, should the latch tab 78 be inadvertently or purposefully biased out of the first opening 62 in the needle guard 60 after the locking flap 102 has been biased to the engaged or locked position as shown in FIG. 9, the forward end of the ledge 79 will contact the locking surface 110 on the locking button 106 to prevent axial movement of the needle guard 60 in the "E" direction and thereby prevent reuse of the needle 56.

The use of the needle guard assembly 40 of the present invention will now be described. If the needle guard assembly is not integrally formed on the syringe body or otherwise permanently attached to the syringe body, it may be safely attached to the syringe 10 by applying a rotational force to the needle guard 60 to screw the hub 42 onto the forward portion of the syringe 10. It will be appreciated that during installation and prior to use, the guard 60 will be in a latched position as illustrated in FIG. 8. If the syringe 10 is not pre-filled with medicament, the user simply biases the latch tab 78 out of the latch opening 62 in the needle guard 60 and applies an axial force to the needle guard 60 in the "E" direction to retract the needle guard 60 over the syringe body 12 to thereby expose the injection end 57 of the needle 56. Thereafter, the injection end 57 of the needle 56 may be inserted through a rubber diaphragm in a medicament vial (not shown) and the medicament may be drawn through the needle 56 into the syringe body 12 by withdrawing the plunger rod 16 in the 'A" direction until a desired amount of medicament has been drawn into the syringe 10. Thereafter, the needle guard 60 is moved back to the latched position wherein the needle 56 is entirely received within the guard 60. The user can then safely transport the syringe and needle guard assembly to the patient without risk of contaminating the needle 56 and without risk of an inadvertent needle stick. To make the first injection, the needle guard 60 is unlatched in the above-mentioned manner to expose the injection end 57 of the needle 56. The injection is then carried out in a conventional manner. After the injection has been completed, the needle guard 60 may be returned to the latched position (FIGS. 7 and 8). If further injections are required at a later time, the needle guard 60 protects the needle 56 from becoming contaminated between injections and also protects the user from exposure to the needle. After all injections have been completed, the needle guard 60 may be locked in a permanent extended position by pressing the locking tab 106 until the locking flap 102 snaps under the forward ledge 79 portion of the latch tab 78. In some embodiments, an audible "click" may be heard. The locking flap 102 serves to bias the latch tab 78 into the latch opening 62 in the needle guard 60. Furthermore, should someone attempt to retract the needle guard 60 after the locking flap 102 has been pressed into such "fail safe" position, the latch tab 78 will contact the locking surface 110 on the locking tab 106 to thereby prevent retraction of the needle guard 60.

Figure 10:
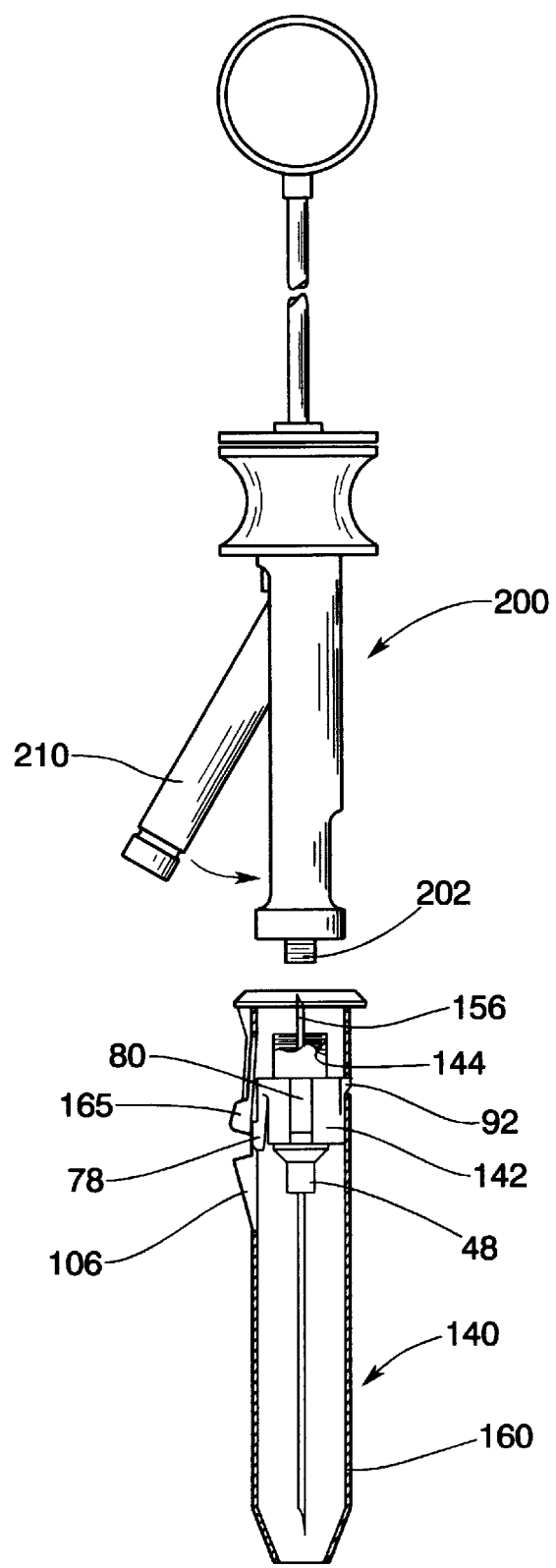
FIG. 10 is an exploded assembly view of another needle guard assembly of the present invention and a conventional dental syringe.

While the above-described embodiment of the present invention is particularly-well suited for use with syringes ranging in size from 1 mm, 3 mm, 5 mm, etc. and that have a luer-lock attachment portion, the artisan of ordinary skill will appreciate that the present invention may be used with a variety of other types and sizes of conventional syringes known in the art. For example, as shown in FIG. 10, the present invention may be used in connection with a conventional dental syringe 200. In this embodiment, however, the needle guard assembly 140 is constructed in the manner described above with respect to the needle guard assembly 40 except that the hub 142 has a threaded port 144 formed therein for receiving the threaded nose portion 202 of the syringe 200. In addition, the needle 156 protrudes out of the threaded port 144 to enable it to pierce the diaphragm of a medicament-filled ampoule 210 in a known manner. The other features of the needle guard assembly 140 are otherwise identical to the features of the needle guard assembly 42 and have been labeled herein with similar element numbers.

It is apparent from the foregoing discussion that the present invention addresses the shortcomings of prior needle guard assemblies. The present invention enables a hypodermic needle to be safely attached to a syringe and transported by the user without risk of an inadvertent needle stick or without contaminating the needle. The needle guard of the subject invention can also be permanently locked in position to prevent further use of the needle and to facilitate safe disposal of the needle. In addition, the subject invention is easy to use and can be economically fabricated. Those of ordinary skill in the art will, of course, appreciate that various changes in the details, materials and arrangement of parts which have been herein described and illustrated in order to explain the nature of the invention may be made by the artisan of ordinary skill within the principle and scope of the invention as expressed in the appended claims.

What is claimed is:

1. A needle assembly for a syringe having a syringe body, said needle assembly comprising:
   a needle-supporting hub attachable to the syringe body, said needle-supporting hub having a needle protruding therefrom and a latch assembly formed thereon;
   a hollow needle guard slidably supported on said needle-supporting hub, said hollow needle guard being selectively movable between a first extended position covering said needle protruding from said needle-supporting hub and a second retracted position wherein an end of said needle is exposed;
   a latch opening in a portion of said hollow needle guard through which a portion of said latch assembly can selectively extend such that said portion of said latch assembly is selectively biasable between a first engaged position wherein a portion of said latch assembly is received in said latch opening to retain said hollow needle guard in said first extended position and a second disengaged position wherein said portion of said latch assembly is biased out of said latch opening in said hollow needle guard to enable said hollow needle guard to be moved to said second retracted position; and
   a locking mechanism formed in said hollow needle guard, said locking mechanism being selectively biasable between a first unlocked position and a second locked position wherein a portion of said locking mechanism engages a portion of said latch assembly to permanently retain said hollow needle guard in said first extended position.

2. The needle assembly of claim 1 wherein said latch assembly comprises:
   a latch flap formed in said needle supporting hub; and
   a latch tab formed on an end of said latch flap and sized to be selectively received in said latch opening in said hollow needle guard.

3. The needle assembly of claim 2, further comprising an actuator flap formed in a wall of said hollow needle guard, a portion of said actuator flap in registration with said latch tab when said hollow needle guard is in said first extended position.

4. The needle assembly of claim 3 further comprising an actuator button formed on said actuator flap.

5. The needle assembly of claim 2 wherein said locking mechanism comprises:
   a locking flap formed in a wall portion of said hollow needle guard, wherein a portion of said locking flap is selectively biasable under a portion of said latch flap to achieve said second locked position.

6. The needle assembly of claim 5 further comprising a locking tab on an exterior portion of said locking flap to enable said portion of said locking flap to be biased under said portion of said latch flap and into a locked position.

7. The needle assembly of claim 6 wherein said locking tab abuts said latch flap when said locking tab is in said locked position to prevent said hollow needle guard from being slidable to said second retracted position.

8. The needle assembly of claim 7 wherein said latch tab further has a ledge formed thereon for receiving a portion of said locking flap thereon when said hollow needle guard is in said first extended position and said locking flap is in said unlocked position.

9. The needle assembly of claim 1 wherein said needle-supporting hub has a threaded port therein for threaded attachment to the syringe body.

10. The needle assembly of claim 1 wherein said needle-supporting hub has a luer-lock fitting formed thereon for removable attachment to the syringe body.

11. The needle assembly of claim 1 wherein said needle supporting hub is fabricated from nylon and said hollow needle guard is fabricated from PETG.

12. A disposable hypodermic needle assembly for a syringe having a syringe body, said disposable hypodermic needle assembly comprising:
   a needle-supporting hub attachable to the syringe body and supporting therein a needle having an injection end;
   a selectively biasable latch flap in said needle-supporting hub, said latch flap having a latch tab formed on one end thereof;
   a hollow needle guard slidably supported on said needle-supporting hub, said hollow needle guard being selectively movable between a first extended position covering said injection end of said needle and a second retracted position wherein said injection end of said needle is exposed;
   a latch opening through a portion of said hollow needle guard for selectively receiving therein said latch tab on said latch flap when said needle guard is in said first extended position to latch said needle guard in said first extended position; and
   a locking flap formed in a wall portion of said needle guard and in confronting relationship with said latch flap when said needle guard is in said first extended position, said locking flap being biasable into permanent locking engagement with said latch flap to retain said latch tab in said latch opening in said hollow needle guard to thereby permanently retain said hollow needle guard in said first extended position.

13. The needle assembly of claim 12 wherein said locking flap has an outwardly protruding locking tab thereon that confronts said latch flap when said locking flap is in permanent locking engagement with said latch flap.

14. The needle assembly of claim 12 wherein said latch tab further has a ledge formed thereon for receiving a portion of said locking flap thereon when said hollow needle guard is in said first extended position and said locking flap is in an unlocked position and wherein said portion of said locking flap is biasable under said ledge to permanently retain said locking flap in locking engagement with said latch flap.

15. The needle assembly of claim 12 further comprising an actuator flap formed in a wall of said hollow needle guard, a portion of said actuator flap in registration with said latch tab when said hollow needle guard is in said first extended position.

16. The needle assembly of claim 15 further comprising an actuator button formed on said actuator flap to enable said actuator flap to be biased into engagement with said latch tab to bias said latch tab out of said latch opening in said portion of said hollow needle guard.

17. The needle assembly of claim 12 further comprising:
   a retainer flap formed in said hub and diametrically opposed to said latch flap, said retainer flap having a retainer tab formed thereon; and
   a retainer opening in said hollow needle guard for selectively receiving said retainer tab therein when said hollow needle guard is in said first extended position.

18. The needle assembly of claim 17 wherein said latch tab has a first width and wherein said retainer tab has a second width that is less than said first width.

19. The needle assembly of claim 17 wherein said retainer tab has a sloped forward edge.

20. A hypodermic needle assembly for a syringe having a syringe body, said hypodermic needle assembly comprising:
   a needle-supporting hub attachable to the syringe body and supporting a needle therein that has an injection end;
   a selectively biasable latch flap in said needle supporting hub, said latch flap having a latch tab formed on one end thereof, said latch tab being offset from an end of said latch flap to define a ledge thereon;
   a hollow needle guard slidably supported on said needle-supporting hub, said hollow needle guard being selectively movable between a first extended position covering said injection end of said needle and a second retracted position wherein said injection end of said needle is exposed;
   a latch opening through a portion of said hollow needle guard for selectively receiving therein said latch tab on said latch flap when said needle guard is in said first extended position;
   an actuator flap formed in a wall of said hollow needle guard, a portion of said actuator flap in registration with said latch tab when said hollow needle guard is in said first extended position, said actuator flap having an actuator button thereon to enable said actuator flap to be biased into engagement with said latch tab to bias said latch tab out of said latch opening in said portion of said hollow needle guard to enable said hollow needle guard to be moved to said second retracted position;
   a locking flap formed in a wall portion of said needle guard and in confronting relationship to said latch flap when said needle guard is in said first extended position, said locking flap being biasable into permanent locking engagement with said latch flap to permanently retain said hollow needle guard in said first extended position, said locking flap having an outwardly protruding locking tab thereon that confronts said latch flap when said locking flap is in permanent locking engagement with said latch flap to prevent said hollow needle guard from being moved to said second retracted position.

21. A needle assembly for a syringe having a syringe body, said needle assembly, comprising:
   means for supporting a needle, said means for supporting a needle being removably attachable to a syringe body and supporting a needle having an injection end;

means for selectively shielding said injection end of said needle, said means for selectively shielding being slidably supported on said means for supporting and being selectively movable between a first extended position covering said injection end of said needle and a second retracted position wherein said injection end of said needle is exposed;

means for selectively latching said means for selectively shielding in said first extended position;

a latch opening through a portion of said hollow needle guard through which a portion of said means for selectively latching can selectively extend such that said portion of said means for selectively latching is selectively biasable between a first engaged position wherein said means for selectively latching extends into said latch opening to retain said means for selectively shielding in said first extended position and a second disengaged position wherein said means for selectively latching is biased out of said first opening to permit said means for selectively shielding to be moved to said second retracted position; and a means for permanently locking said means for selectively shielding in said first extended position, said means for selectively locking formed on said means for selectively shielding and being selectively biasable between a first unlocked position and a second locked position wherein a portion of said means for selectively locking engages a portion of said means for selectively latching to permanently retain said means for selectively shielding in said first extended position.

22. A hypodermic syringe, comprising:

a hollow syringe body having a forward end and a rear end;

a plunger rod slidably received in said hollow syringe body;

a piston slidably received in said hollow syringe body and attached to an end of said plunger rod;

a needle-supporting hub on said front end of said hollow syringe body and supporting a needle having an injection end therein;

a selectively biasable latch flap in said needle-supporting hub, said latch flap having a latch tab formed on one end thereof, said latch tab being offset from an end of said latch flap to define a ledge thereon;

a hollow needle guard slidably supported on said needle-supporting hub, said hollow needle guard being selectively movable between a first extended position covering said injection end of said needle and a second retracted position wherein said injection end of said needle is exposed;

a latch opening through a portion of said hollow needle guard for selectively receiving therein said latch tab on said latch flap when said needle guard is in said first extended position;

an actuator flap formed in a wall of said hollow needle guard, a portion of said actuator flap in registration with said latch tab when said hollow needle guard is in said first extended position, said actuator flap having an actuator button thereon to enable said actuator flap to be biased into engagement with said latch tab to bias said latch tab out of said opening in said portion of said hollow needle guard to enable said hollow needle guard to be moved to said second retracted position;

a locking flap formed in a wall portion of said needle guard and in confronting relationship to said latch flap when said needle guard is in said first extended position, said locking flap being biasable into permanent locking engagement with said latch flap to permanently retain said hollow needle guard in said first extended position, said locking flap having an outwardly protruding locking tab thereon that confronts said latch flap when said locking flap is in permanent locking engagement with said latch flap to prevent said hollow needle guard from being movable to said second retracted position.

23. A method of selectively shielding a needle of a hypodermic syringe having a syringe body that supports an actuatable plunger rod and piston therein, said method comprising:

attaching a needle-supporting hub to an end of the syringe body, the needle-supporting hub supporting a needle and having a latch assembly formed therein and a hollow needle guard slidably supported thereon for selective movement between a first extended position covering an injection end of the needle and a second retracted position exposing the injection end of the needle, the hollow needle guard having a latch opening therein through which a portion of the latch assembly can selectively extend such that a portion of the latch assembly is selectively biasable between a first engaged position wherein the latch assembly protrudes into the latch opening to retain the hollow needle guard in the first extended position and a second disengaged position wherein the latch assembly is biased out of the latch opening to enable the hollow needle guard to be moved to the second retracted position, the hollow needle guard further having a locking mechanism formed therein and being selectively biasable between a first unlocked position and a second locked position wherein a portion of the locking mechanism engages a portion of the latch assembly to permanently retain the hollow needle guard in the first position, the latching assembly being in the first engaged position during said attaching;

unlatching the latch assembly from the first engaged position;

moving the needle guard to the second retracted position to expose the injection end of the needle;

loading a medicament into the syringe;

injecting medicament into a patient;

withdrawing the needle from the patient;

moving the hollow needle guard to the first extended position;

re-latching the latch assembly into the first engaged position; and biasing the locking mechanism into permanent locking engagement with the latching assembly.

24. A method of selectively shielding a needle of a hypodermic syringe having a syringe body that supports an actuatable plunger rod and piston therein, said method comprising:

attaching a needle-supporting hub to an end of the syringe body, the needle-supporting hub having a latch assembly formed therein and a hollow needle guard slidably supported thereon for selective movement between a first extended position covering an injection end of the needle and a second retracted position exposing the injection end of the needle, the hollow needle guard having a latch opening therein through which a portion of the first latch assembly can selectively extend such that a portion of the latch assembly is selectively biasable between a first engaged position wherein the latch assembly protrudes into the latch opening to retain the hollow needle guard in the first extended position and a second disengaged position wherein the latch assembly is biased out of the first opening to permit the hollow needle guard to be moved to the second retracted position, the hollow needle guard further having a locking mechanism formed therein and being selectively biasable between a first unlocked position and a second locked position wherein a portion of the locking mechanism engages a portion of the latch assembly to permanently retain the hollow needle guard in the first position, said latching assembly being in the first engaged position during said attaching;

unlatching the latch assembly from the first engaged position;

moving the needle guard to the second retracted position to expose the injection end of the needle;

loading a medicament into the syringe;

injecting a portion of the medicament into a patient;

withdrawing the needle from the patient;

moving the hollow needle guard to the first extended position;

re-latching the latch assembly to the first engaged position;

unlatching the latch assembly a second time from the first engaged position;

moving the needle guard to the second retracted position to expose the injection end of the needle a second time;

injecting another portion of the medicament into the patient;

withdrawing the needle from the patient;

moving the hollow needle guard to the first extended position;

re-latching the latch assembly to the first engaged position; and biasing the locking mechanism into permanent locking engagement with the latching assembly.

* * * * *